(12) United States Patent
Mosbaugh

(10) Patent No.: US 6,769,271 B2
(45) Date of Patent: Aug. 3, 2004

(54) METHOD OF MAKING AN AGGLOMERATION OF FUSED MICROSPHERES

(75) Inventor: Jim Mosbaugh, Tampa, FL (US)

(73) Assignee: Tatho Materials, Inc., Tampa, FL (US)

( * ) Notice: Subject to any disclaimer, the term of this patent is extended or adjusted under 35 U.S.C. 154(b) by 192 days.

(21) Appl. No.: 09/779,175

(22) Filed: Feb. 8, 2001

(65) Prior Publication Data

US 2001/0008318 A1 Jul. 19, 2001

Related U.S. Application Data

(62) Division of application No. 09/302,270, filed on Apr. 30, 1999, now Pat. No. 6,245,733.

(51) Int. Cl.$^7$ .............................. C03B 19/09; A61K 7/46
(52) U.S. Cl. ................. 65/17.3; 65/66; 512/4; 264/117; 264/119; 106/601
(58) Field of Search ....................... 65/17.3, 66; 512/4; 264/117, 119; 106/601

(56) References Cited

U.S. PATENT DOCUMENTS

| | | |
|---|---|---|
| 3,365,315 A | 1/1968 | Beck et al. |
| 3,985,298 A | 10/1976 | Nichols |
| 4,155,897 A | 5/1979 | Schlusener |
| 4,788,164 A | 11/1988 | Che et al. |
| 5,149,474 A * | 9/1992 | Rohatyn ..................... 264/220 |
| 5,336,665 A | 8/1994 | Garner-Gray et al. |
| 5,387,439 A | 2/1995 | Roberts |
| 5,534,348 A | 7/1996 | Miller et al. |
| 5,573,984 A | 11/1996 | Breitenbucher et al. |
| 5,725,869 A | 3/1998 | Lo |
| 5,824,345 A | 10/1998 | Milstein |
| 5,849,055 A | 12/1998 | Arai et al. |
| 5,871,722 A | 2/1999 | Nacht et al. |
| 6,245,733 B1 * | 6/2001 | Mosbaugh ..................... 512/1 |
| 6,489,047 B2 * | 12/2002 | Mosbaugh ................. 264/117 |

* cited by examiner

*Primary Examiner*—Jill Warden
*Assistant Examiner*—Monique T. Cole
(74) *Attorney, Agent, or Firm*—Dennis L. Cook, Esq.

(57) ABSTRACT

A method of making a fragrance delivery system comprising forming fused microspheres and incorparting a fragrance therein. The method relates to the mixing together of two separate factions comprising a silicate part and a modifier part, drying the mixture, heating the mixture to form an agglomeration, removing any free-flowing spheres from the agglomeration, soaking the agglomeration in fragrances or essential oils, and then drying the agglomeration.

6 Claims, No Drawings

METHOD OF MAKING AN AGGLOMERATION OF FUSED MICROSPHERES

CROSS-REFERENCE TO RELATED APPLICATION

The present application is a division of application Ser. No. 09/302,270, filed on Apr. 30, 1999 now U.S. Pat. No. 6,245,733 and titled "Arificial Rock Fragrance Delivery System," by Jim Mosbaugh. application Ser. No. 09/302,270 has been allowed but has not yet issued. The present application claims the benefit of application Ser. No. 09/302,270 and incorporates the contents by reference.

BACKGROUND OF THE INVENTION

1. Field of the Invention

The present invention relates to a method for making fragrance delivery systems. In particular, the invention relates to a method of making pre-glass agglomerations that adsorb fragrance producing oils and volatiles, and releases the fragrance innate to the oils and volatiles over an extended period of time without being messy or wet.

2. Description of the Related Art

Most delivery systems that utilize microspheres are manufactured out of acrylates or nonsiliceous polymers. There are no fragrance delivery systems that utilize soda lime borosilicate microspheres fused together naturally without additives. Most fragrance systems have a short life span and lose their aroma within a few months. Virtually no currently available fragrance systems last for longer than a few months under any circumstances. Most also have a very intense smell initially with a reasonably pleasant odor after a few weeks which fades fairly fast.

Microspheres have been used in the past for a variety of purposes. The most common uses pertain to holders for chemicals in compositions such as holding fragrance for laundry detergent In other words, the microspheres contain a chemical and are mixed with other compounds to form a heterogeneous composition where the microspheres will release the chemicals either gradually or all at once in response to a stimulus such as a change in ionic character, heat or other stimulus. Microspheres are also used in drug delivery systems designed to release the drug contained in the microsphere at a particular time according to pH or other factor.

The material and use of the pre-glass agglomeration created by this invention are unique and unknown in the past. Also, these pre-glass agglomerations are not discrete spheres but rather modified soda-lime borosilicate sphere clusters, wherein thousands of microspheres become molecularly fused together via microcrystalline like structures on the sphere surfaces. Therefore, this invention provides a method of making a microsphere matrix without the addition of costly binders and polymers. These microcrystalline structures are distinctly different from current available industrially manufactured microspheres.

U.S. Pat. No. 3,365,315 issued to Beck, et al. on Jan. 23, 1968, discloses glass bubbles made from glass cullet particles by heating. This amorphous solid contains $SiO_2$ (60–80%), $Na_2O$ (5–26%), CaO (5–25%), $K_2O/Li_2O$ (5–16%), and $Na_2O/K_2O/Li_2O$ (5–16%) plus some other oxides. The temperature range utilized for bubble formation is between 1050° and 1300° C. The resultant amorphous solid can be utilized as ingredients in molded parts designed for use in high pressure environments. These particles also have the capacity be used with thin walls thus possessing a maximum strength and crushable if that strength is exceeded. The methods utilized to make the glass bubbles taught by Beck, as well as the glass bubbles themselves, are very different from the rock of the present invention.

U.S. Pat. No. 3,985,298 issued to Nichols on Oct. 12,1976, discusses controlled release materials, and method of using, that can be incorporated into a chemical delivery system. The materials utilized by Nichols are polymer-liquid composite materials which may contain 99% or more of the liquid. These controlled release materials can be incorporated into aerosol propellants, food products, chewing gum, pharmaceutical compounds, agricultural products, or cosmetic preparations. The desired functions of the release materials are flavoring, scent, coloring, medication, is dermatological action, pesticidal action, or agricultural fertilizer. The materials and objectives utilized by Nichols are different from the present invention.

U.S. Pat. No. 4,155,897 issued to Schlusener on May 22, 1979, discloses compositions exhibiting controlled release of an active substance. The compositions of Schlusener comprise an unsaturated polyester resin, an active substance, hollow microspheres of an organic material, and an inorganic material. The hollow microspheres can be made of glass and are mixed with an unsaturated polyester resin to make a molded solid or semisolid substance. An active ingredient, such as volatile oils, is added to the substance. The strength of the final product depends on the unsaturated polyesters used, but is less than the strength of the unsaturated polyester used because the hollow microspheres reduce the overall strength. The composition taught by Schlusener, and the method of making the composition, are different from the amorphous rock of the present invention, and the method of making it. The release of gas by the molded item is measured by a period of up to about half a year which is significantly less than the year and a half capacity of the present invention. There is a relatively high gas release rate the first week, less the next three weeks and even less for the remainder of the active time. Also, the compositions of Schlusener lacks the strength and low density combination of the present invention.

U.S. Pat. No. 5,336,665 issued to Garner-Gray, et al. On Aug. 9, 1994, discloses a hydrophobic porous inorganic carrier particle having a perfume absorbed into the particle. In particular, a detergent composition containing the carrier particle and a method for manufacturing the same is disclosed. The inorganic carriers used in Gamer-Gray include aluminosilicates such as certain zeolites, clays, aluminas and silicas, all of which are chemically treated or naturally hydrophobic. These porous, inorganic carrier particles are not designed to release odor over an extended period of time, but to deliver perfume to clothing or other surface via a detergent or the like. The particles used in Garner-Gray are not designed for room deodorizers, are not strong, and are not exceptionally adsorbent in that they are hydrophobic and would not adsorb water or alcohols.

U.S. Pat. No. 5,725,869 issued to Lo on Mar. 10, 1998, describes microsphere reservoirs for controlled release applications. The microspheres, optionally containing an ingredient to be dispensed through controlled release, are prepared by solvent evaporation of an oil-in-water emulsion formed from an organic solvent containing a polymer and a plasticizer and an aqueous solution containing one or more emulsifying agents. The microcapsules formed are porous and spongy in structure as opposed to hollow. These microspheres have a relatively high load rate and a low dispersion rate. They are useful for agricultural chemicals, pharmaceuticals, cosmetics and fragrances. The invention of Lo is not designed to be a room deodorizer, and does not have a sturdy solid nature as does the rock of the current invention.

U.S. Pat. No. 5,824,345 issued to Milstein on Oct. 20, 1998, discloses compositions useful in the delivery of fragrances and flavorants. A method for preparing the compositions is disclosed: the active agent is mixed with the proteinoid of hydrolyzed vegetable protein solution and the proteinoid or modified hydrolyzed vegetable protein is precipitated out of the solution, thereby forming a microsphere containing the active agent. The product formed by the method in Milstein differs from the present invention in that the present invention adsorbs any liquid, oil or alcohol, while Milstein requires the microspheres to be made concurrent with placing the agent therein which is a handicap in that it reduces the usefulness of the Milstein invention. Also, the microsphere of Milstein is not as sturdy as the current invention and the aroma does not last nearly as long.

U.S. Pat. No. 5,849,055 issued to Arai, et al. on Dec. 15, 1998, discloses a process for making inorganic microspheres which comprises pulverizing a material by wet pulverization to obtain a slurry of a pulverized powder material, spraying the slurry to form liquid droplets, and heating the liquid droplets to fuse or sinter the powder material to obtain inorganic microspheres. These microspheres are discrete individual microbeads and cannot be utilized in the manner of the present invention. The microspheres of Arai can be used as a powder or an ingredient, but not as a deodorizing rock.

U.S. Pat. No. 5,871,722 issued to Nacht, et al. on Feb. 16, 1999, shows ionic beads usefully for controlled release and adsorption. Active ingredients are released from the ionic polymer beads over an extended period of time such as when orally administered, or when applied to a keratinic material, typically human skin or hair, or when otherwise delivered to a target environment. Clearly, the ionic beads of Nacht are designed to deliver an active ingredient upon contact with some substance which releases their ionic bonds. These ionic beads would not be useful for room deodorants or absorption of oils.

U.S. Pat. No. 5,534,348 issued to Miller, et al. on Jul. 9, 1996, describes hollow borosilicate microspheres and a method of making them. The compositions of the sodium borosilicate starts with the preferred weight ratio of $Na_2O:SiO_2:B_2O_3$ between 1.0:2.5:0.2 and 1.0:3.22:0.5 for the starting material. The borosilicate microspheres of Miller are used in reflective paints and coatings, incorporated into molded plastic products, and f or use as thermal insulation, but not as delivery vehicles for scents or as adsorbent materials.

None of the above inventions and patents, taken either singularly or in combination, is seen to describe the instant invention as claimed. Thus, a method of making an artificial rock fragrance delivery system solving the aforementioned problems is desired.

SUMMARY OF THE INVENTION

The current invention is a method for making a pre-glass agglomeration that acts as a vector for fragrance delivery by utilizing fused, microspheres with calcium integrated into the spheres from an aqueous sol precursor. The artificial fragrance delivery system is also referred to herein as an artificial rock fragrance delivery system, because the pre-glass agglomeration resembles a rock or rock-like structure. The fragrance delivery system has an extended fragrance release time generally exceeding a year and a half. The pre-glass agglomeration uses microcapillary action to quickly uptake oils and alcohols to more than double the weight of the pre-glass agglomeration. Also, the slow release of a fragrance without any residual liquid escape is another advantageous quality of the instant pre-glass agglomeration invention. It is also possible to recharge or replenish the pre-glass agglomerations an unlimited number of times with additional fragrance oils/alcohols after the odor fades. The pre-glass agglomerations can also be molded into a variety of shapes using conventional vacuum applications to maintain the integrity of the resulting molded shape.

The pre-glass agglomerations with fragrance can be used for aromatherapy crock pots or boilers. They may also be dipped in flammable oils and used as incense or candle wicks. The pre-glass agglomerations can be used as room or facility fragrances, to counteract pungent odors, and may be colored or dyed as desired.

The pre-glass agglomerations can also be used for various filtration applications. For example, they can be used for anionic and cationic separation by modification of the metal groups in order to bind salts from brine discharge in desalinization plants to economically reduce salt content. The pre-glass agglomerations can be used for separation filters for chemical processes such as removal of chlorine or sulfates from stacks. The surfaces, internal and external, of the pre-glass agglomerations can be modified by various acylations or substitutions to provide functional groups which can aid in separations, chemical collections and catalysis. Additional separation methods include the use of the rocks in saline/petroleum separation with for example oil spills.

There are numerous other uses as well. They can be used as low weight buoyancy control devices due to their extremely low density, and utilized as heat insulation and/or fire-resistant filler material. Also, they can be used as insect repellent by soaking the pre-glass agglomeration, having increased borate content, in citronella, lavender or other repellant. Sodium bicarbonate can be adsorbed by these rocks to produce fizzing in an essential oil bath. Naked or untreated pre-glass agglomerations can be used to adsorb various airborne chemical vapors, for example in nail salons and urethane production facilities.

Additionally, prior to high temperature processing, the powder may be applied to various fabrics in order to achieve waterproofing characteristics. Thermal and sound insulation benefits also result. It is notable that in order to achieve flexibility from the coated fabric it is necessary to incorporate various drying control chemical additives. The treated fabric is excellent for aeronautical applications such as the insulation barrier between the fuselage and the exterior of airplanes. Accordingly, it is a principal object of the invention to provide a method of making an agglomeration of pre-glass material that has exceptional absorption qualities, and is dry to the touch once dried and removed from the fluid to be adsorbed.

It is another object of the invention to provide a method of making an agglomeration of pre-glass material that can adsorb oils and other lipophilic substances readily without significant mess. It is a further object of the invention to provide a method of making an agglomeration of pre-glass material that can adsorb alcohol-based liquids readily. Still another object of the invention is to provide a method of making an agglomeration of pre-glass material that after absorption of an aromatic oil/alcohol-based substance will release the fragrance of the adsorbed substance over an extended period of time. It is an object of the invention to provide a method of making improved elements and arrangements thereof for the purposes described which is inexpensive, dependable and fully effective in accomplishing its intended purposes. These and other objects of the present invention will become readily apparent upon further review of the following specification.

DETAILED DESCRIPTION OF THE PREFERRED EMBODIMENTS

The present invention pertains to a highly adsorbent pre-glass agglomeration or rocks which can be utilized in diverse ways. The pre-glass agglomeration can be used to adsorb oil/alcohol-based liquids. Upon absorption of liquids, the surface of the pre-glass agglomeration is dry to the touch, thus eliminating any potential mess or stickiness. The pre-glass agglomeration is a long term fragrance delivery system that will adsorb aromatic oil/alcohol based liquids, and then release the fragrance of the aromatic liquid slowly over a sustained period of time, generally up to about one and a half years.

Colored liquid(s) and/or dye(s) can be used to decorate the pre-glass agglomeration, wherein the resulting pre-glass agglomeration has the color or dye of the liquid adsorbed therein. Also, the pre-glass agglomeration can be formed into various shapes as desired. Other applications include salt binding, filtration, separation and insulation. As used herein, all percentages (%) are percent weight in volume of water prior to heating, also expressed as weight/volume %, %(w/v), w/v, w/v % or simply %, unless otherwise indicated. The following example is the preferred embodiment of the pre-glass agglomeration according to the present invention. It should be noted, however, that the example is by no means a limitation of the invention, and that various modifications and improvements in the manufacturing process all fall under the scope of this invention.

EXAMPLE 1

$SiO_2$ from about 60 to about 75%;

$Na_2O$ from about 10 to about 35%;

$K_2O$ from about 2 to about 20%;

$B_2O_3$ from about 5 to about 20%; and

CaO from about 0.5 to about 12%

Preferably, commercial silicates are utilized such as sodium silicate having a weight ratio 3.22, or sodium silicate modified with a caustic agent or acetate having a weight range between 2.8–3 silicate to alkali, or potassium silicates such as KASIL (PQ Corporation) having a weight ratio 2.44 are used. Modifiers such as tech grade boric acid and calcium nitrate are also used. The slurry for the modifiers is approximately 8–18% solids. The total solution is between 20–40% solids. Other modifiers may be added in quantities from about 1–10% These other modifiers may include Pb, MgO, $Al_2O_3$, BaO, $Li_2O$, Ge, and S.

A preferred method of making the pre-glass agglomeration of Example 1 comprises the following steps: The constituents are mixed together in two separate factions comprising the silicate part and the modifier part. The modifier part is boric and calcium in an aqueous slurry. The modifier solution is either poured into the silicate solution with vigorous mixing or the two are mixed together using an impeller pump with a recirculation loop. Vigorous mixing and slow addition of the boric/calcium solution are essential.

The solution, once mixed together, has a pH of 10–12. Mixing temperatures approach 60° C. This solution is fed to a two fluid nozzle for atomization via a diaphragm pump at 25–200 psi. Alternatively, a centrifugal atomizer may be utilized at 10,000–25,000 rpm. While air atomizing, air pressure varies between 80–1000 psi. The drying step occurs at about 100° C. to about 300° C. The outlet temperature is 300–800° F.

The spray-dried product is then fed via pneumatic conveyor to a rotary tube furnace. The powder is fed into the furnace via an Accurate Feeder to a 316 SS tube rotating at 7–12 rpm and an angle of repose approximately ⅛ to 5 inches per foot. The furnace has 4 discrete zones with a temperature profile from 200° C. to 1200° C. with either a co-current or a counter current dry air flow at approximately 25–200 SCFH. Another atmosphere which is reducing, for example methane, may be used.

The pre-glass agglomeration is then collected from the furnace and sifted to remove any free flowing spheres from the pre-glass agglomeration. As a result of the sifting, the pre-glass agglomeration takes on a smooth surface. Examination under 40× microscopy indicated thousands of fused spheres.

The pre-glass agglomeration, once formed, is dipped into a solution containing various fragrance(s) or essential oils and allowed to soak for approximately 20–30 minutes. Conversely, the pre-glass agglomeration can be placed in a shallow dish of oils and inserted into a high pressure oven at ambient temperatures to reduce absorption time. The oils may also be dyed to impart color to the finished rock. The pre-glass agglomeration is removed from the dip via a screening process and conveyed under a series of ultraviolet heat lamps in order to dry the pre-glass agglomeration to the touch.

Oils used in the absorption process are preferably cut with a carrier such as dipropylene glycol, propylene glycol, SD alcohols, etc. Pre-glass agglomerations to be used in contact with the skin will use only FDA approved carriers and oils.

Pre-glass agglomerations made by the above method can also be used to separate oil from saline. Pre-glass agglomerations which have not been soaked in a fragrance containing liquid are preferably used for this.

In order to separate oil from saline the pre-glass agglomerations are placed in an oil and water dispersion and are mixed either by tidal action or paddle. Allow the agglomerations to soak for up to 48 hours and then collect the agglomerations with a screen or net. Place the agglomerations in either a conventional oven or a vacuum oven in order to reclaim the petroleum. The reclaimed petroleum can then be recycled. The agglomerations can be discarded or reused. To reuse, the agglomerations must be washed with a low weight alcohol.

It is to be understood that the present invention is not limited to the embodiments described above, but encompasses any and all embodiments within the scope of the following claims.

I claim:

1. A process for making an agglomeration of fused microspheres comprising the steps of:
    a. mixing silicates;
    b. mixing modifiers;
    c. mixing silicates and modifiers together to form a mixture;
    d. drying the mixture to form a dry resultant material;
    e. heating the resultant material to form an agglomeration;
    f. soaking the agglomeration in a liquid fragrance selected from the group consisting of an oil and an alcohol;
    g. removing the agglomeration from the liquid fragrance; and h. drying the fragrance containing the agglomeration.

2. A process for making an agglomeration of fused microspheres as in claim 1, wherein:

said silicates are sodium silicate and potassium silicate; and said modifiers are boric acid, Pb, MgO, $Al_2O_3$, BaO, $Li_2O$, Ge, S and calcium nitrate.

3. A process for making an agglomeration of fused microspheres as in claim 1, wherein:
   a. the step of mixing the silicates and the modifiers together to form the mixture occurs by pouring the modifiers into the silicates;
   b. the step of drying occurs with a spray dryer via a diaphragm pump at 50–150 psi and atomizing at 80 to 300 psi with outlet temperature ranging from about 300° to about 800° F.; and
   c. the step of heating the resultant material occurs in a furnace by an accurate feeder rotating 5–20 rpm at an angle of repose ⅛–5 inches per foot at about 200° C. to about 1200° C. with a counter current dry air flow 25–200 SCFH.

4. A process for making an agglomeration of fused microspheres as in claim 2, wherein:
   a the step of mixing the silicates and the modifiers together to form the mixture occurs by pouring the modifiers into the silicates;
   b. the step of drying occurs with a spray dryer via a diaphragm pump at 56–150 psi and atomizing at 80 to 300 psi with outlet temperature ranging from about 300° to about 800° F.; and
   c. the step of heating the resultant material occurs in a furnace by an accurate feeder rotating 5–20 rpm at an angle of repose ⅛–5 inches per foot at about 200° C. to about 1200° C. with a co-current dry air flow 25–200 SCFH.

5. A process for making an agglomeration of fused microspheres as in claim 2, wherein:
   a. the step of mixing the silicates and the modifiers occurs by an impeller pump and a recirculation loop;
   b. the step of drying occurs with a spray dryer with a diaphragm pump at 25–200 psi and air atomizing at 80 to 800 psi with an outlet temperature ranging from about 300° to about 800° F.; and
   c. the step of heating the resultant material occurs in a furnace by an accurate feeder rotating 5–20 rpm at an angle of repose ⅛–5 inches per foot at about 200° C. to about 1200° C. with a co-current dry air flow 25–200 SCFH.

6. A process for making an agglomeration of fused microspheres as in claim 2, wherein:
   a. the drying steps occurs at about 1000 to about 300° C.; and
   b. the step of heating the resultant material occurs in a furnace by an accurate feeder rotating 5–20 rpm at an angle of repose ⅛–5 inches per foot at about 200° C. to about 1200° C. with a co-current dry air flow 25–200 SCFH.

* * * * *